United States Patent
Forbes

(10) Patent No.: US 9,603,564 B2
(45) Date of Patent: Mar. 28, 2017

(54) METHODS AND SYSTEMS FOR ASSESSING PSYCHOLOGICAL CHARACTERISTICS

(75) Inventor: David L. Forbes, Lincoln, MA (US)

(73) Assignee: The Forbes Consulting Group, LLC, Lexington, MA (US)

(*) Notice: Subject to any disclaimer, the term of this patent is extended or adjusted under 35 U.S.C. 154(b) by 896 days.

(21) Appl. No.: 12/713,539

(22) Filed: Feb. 26, 2010

(65) Prior Publication Data

US 2010/0221687 A1    Sep. 2, 2010

Related U.S. Application Data

(60) Provisional application No. 61/156,236, filed on Feb. 27, 2009.

(51) Int. Cl.
| | |
|---|---|
| *G06F 17/00* | (2006.01) |
| *A61B 5/16* | (2006.01) |
| *A61B 5/0484* | (2006.01) |
| *G06F 17/30* | (2006.01) |
| *G06K 9/00* | (2006.01) |
| *G06F 19/00* | (2011.01) |

(Continued)

(52) U.S. Cl.
CPC ............ *A61B 5/165* (2013.01); *A61B 5/0484* (2013.01); *A61B 5/04842* (2013.01); *A61B 5/16* (2013.01); *A61B 5/162* (2013.01); *G06F 17/30032* (2013.01); *G06K 9/00308* (2013.01); *G06F 19/345* (2013.01); *G09B 7/00* (2013.01); *G09B 19/00* (2013.01)

(58) Field of Classification Search
CPC .......... G06Q 30/02; A61B 5/165; A61B 5/16; A61B 5/04842; A61B 5/0484; A61B 5/162; G06F 19/363; G06F 17/30032; G06K 9/00308

USPC .......................................... 434/236, 350, 362
See application file for complete search history.

(56) References Cited

U.S. PATENT DOCUMENTS

| | | | |
|---|---|---|---|
| 6,292,688 | B1 | 9/2001 | Patton |
| 6,826,540 | B1 | 11/2004 | Plantec et al. |
| 7,606,726 | B2 | 10/2009 | Nelson |

(Continued)

FOREIGN PATENT DOCUMENTS

| | | |
|---|---|---|
| CN | 1516561 | 7/2004 |
| CN | 1739451 | 3/2006 |

(Continued)

OTHER PUBLICATIONS

International Search Report and Written Opinion for International Patent Application No. PCT/US2010/025588 dated May 13, 2010.

(Continued)

*Primary Examiner* — Nathan Hillery
(74) *Attorney, Agent, or Firm* — Fish & Richardson P.C.

(57) ABSTRACT

A method for assessing an emotional response from a test subject includes presenting, for a first predetermined period of time, a plurality of stimuli to the test subject through a first computer implemented interface. The method further includes, in response to presenting at least one stimulus, receiving, within a second predetermined period of time, at least one test subject response from the test subject through a second computer implemented interface. The method further includes determining a quantitative emotional profile of the test subject based on the at least one test subject response.

38 Claims, 9 Drawing Sheets

(51) Int. Cl.
*G09B 7/00* (2006.01)
*G09B 19/00* (2006.01)

(56) References Cited

U.S. PATENT DOCUMENTS

| | | | |
|---|---|---|---|
| 7,720,784 B1 | 5/2010 | Froloff | |
| 7,942,816 B2 | 5/2011 | Satoh et al. | |
| 2003/0182123 A1 | 9/2003 | Mitsuyoshi | |
| 2004/0082862 A1 | 4/2004 | Chance | |
| 2004/0210159 A1 | 10/2004 | Kibar | |
| 2005/0054904 A1* | 3/2005 | El-Nokaly | A61B 5/4884 600/300 |
| 2005/0062888 A1 | 3/2005 | Wood et al. | |
| 2005/0209709 A1 | 9/2005 | Bradshaw | |
| 2006/0153531 A1 | 7/2006 | Kanegae et al. | |
| 2006/0229505 A1* | 10/2006 | Mundt | A61B 5/16 600/300 |
| 2007/0050151 A1 | 3/2007 | Satoh et al. | |
| 2007/0066916 A1 | 3/2007 | Lemos | |
| 2008/0037841 A1 | 2/2008 | Ogawa | |
| 2008/0065468 A1 | 3/2008 | Berg et al. | |
| 2008/0097235 A1 | 4/2008 | Ofek et al. | |
| 2008/0101660 A1 | 5/2008 | Seo | |
| 2008/0144882 A1 | 6/2008 | Leinbach et al. | |
| 2008/0255949 A1* | 10/2008 | Genco | A61B 5/0205 705/14.4 |
| 2009/0024049 A1 | 1/2009 | Pradeep et al. | |
| 2009/0083118 A1 | 3/2009 | Kallery et al. | |
| 2009/0275006 A1* | 11/2009 | Cvencek | G09B 7/02 434/236 |
| 2009/0285456 A1 | 11/2009 | Moon et al. | |
| 2010/0009325 A1 | 1/2010 | Afanasiev et al. | |
| 2010/0010317 A1* | 1/2010 | De Lemos | A61B 3/113 600/300 |
| 2010/0055658 A1 | 3/2010 | Sturm et al. | |
| 2010/0145215 A1* | 6/2010 | Pradeep | A61B 5/0484 600/544 |
| 2010/0179950 A1 | 7/2010 | Willcock | |
| 2010/0221687 A1 | 9/2010 | Forbes | |
| 2010/0266213 A1 | 10/2010 | Hill | |
| 2011/0020778 A1 | 1/2011 | Forbes | |
| 2011/0161011 A1* | 6/2011 | Hasson | A61B 5/055 702/19 |
| 2012/0035428 A1 | 2/2012 | Roberts et al. | |
| 2012/0071785 A1 | 3/2012 | Forbes | |
| 2013/0085808 A1 | 4/2013 | Forbes | |
| 2013/0185141 A1* | 7/2013 | Pradeep | A61B 5/0402 705/14.41 |

FOREIGN PATENT DOCUMENTS

| | | |
|---|---|---|
| CN | 103262143 A | 8/2013 |
| EP | 2401733 | 1/2012 |
| EP | 2612312 | 7/2013 |
| IN | 1666/CHENP2013 | 11/2014 |
| RU | 2166280 C2 | 5/2001 |
| RU | 2289310 C2 | 12/2006 |
| RU | 2013114331 | 10/2014 |
| RU | 2595964 C2 | 8/2016 |
| WO | 2007106518 A2 | 9/2007 |
| WO | WO2007/0106083 | 9/2007 |
| WO | WO2008/023260 | 2/2008 |
| WO | WO2010/099443 | 9/2010 |
| WO | WO 2012/030652 | 3/2012 |
| WO | WO 2013/055535 | 4/2013 |
| WO | WO2014/081805 | 5/2014 |

OTHER PUBLICATIONS

International Search Report for PCT/US2011/049383 mailed Dec. 29, 2011.
Cunningham, William A., et al., "The iterative reprocessing model: a multilevel framework for attitudes and evaluation", Social Cognition, vol. 25, No. 5, pp. 736-760, 2007 (25 pages).
Cunningham, William A., et al, "Attitudes to the Right—and Left: Frontal ERP Asymmetries Associated with Stimulus Valence and Processing Goals", ERP Asymmetries in Evaluation, NeuroImage, 28, pp. 827-834, 2005 (30 pages).
Scott, Lisa S., et al., "Electrophysiological Correlates of Facial Self-Recognition in Adults and Children", Cognition, Brain, Behavior, vol. IX(3), pp. 211-238, 2005 (28 pages).
Rudrauf, David, et al., "Enter feelings: Somatosensory responses following early stages of visual induction of emotion", International Journal of Psychophysiology, 72, pp. 13-23, 2009 (11 pages).
Grill-Spector, Kalanit, et al., "Visual Recognition: As soon as you know it is there, you know what it is", Psychological Science, Research Article, American Psychological Society, vol. 16, No. 2, 2005 (9 pages).
Luo, Qian, et al., "Neural dynamics for facial threat processing as revealed by gamma band synchronization using MEG", NIH Public Access, Author Manuscript, PMC Jan. 15, 2008, published Neuroimage, Jan. 15, 2007; 34(2): 839-847 (18 pages).
Rudrauf, David, et al., "Rapid Interactions between Venral Visual Stream and Emotion-Related Structures Rely on a Two-Pathway Architecture", The Journal of Neuroscience, Mar. 12, 2008, 28(11): pp. 2793-2803 (11 pages).
Damasio, Antonio, "Self Comes to Mind: Constructing the Conscious Brain", Pantheon Books, Random House, Inc., copyright 2010 (592 pages).
Cunningham, William A., et al., "Attitudes and evaluations: a social cognitive neuroscience perspective", Science Direct, www.sciencedirect.com 1364-6613/2007 Elsevier Ltd. All rights reserved. doi:10.1016/j.tics.2006.12.2005, TRENDS in Cognitive Sciences, vol. 11, No. 3, pp. 97-104, specifically p. 102, Diagram Box 2, Feb. 7, 2007 (8 pages).
Office action from Australian Application No. 2010217803, issued May 3, 2013 (5 pages).
International Preliminary Report on Patentability for International Patent Application No. PCT/US2010/025588 dated Aug. 30, 2011 (8 pages).
International Search Report and Written Opinion for International Patent Application No. PCT/US2013/070966 dated Feb. 4, 2014 (13 pages).
Office action from Canadian Application No. 2753872 issued Sep. 12, 2013 (3 pages).
Extended European Search Report for EP application No. 10746912.4 issued Sep. 11, 2013 (8 pages).
Examination report from Australian Application No. 2011296331 issued on May 3, 2013 (5 pages).
International Search Report and Written Opinion from PCT application No. PCT/US2012/57943 mailed Jan. 7, 2013 (14 pages).
Schupp, Harald, T. et al., "The selective processing of emotional visual stimuli while detecting auditory targets: An ERP analysis", Brain Research 1230 (2008) pp. 168-176 (9 pages).
Transaction history for U.S. Appl. No. 13/683,729 as of Feb. 24, 2014.
Transaction history for U.S. Appl. No. 12/872,531 as of Feb. 24, 2014.
Transaction history for U.S. Appl. No. 13/249,968 as of Feb. 24, 2014.
Chinese Office action with English translation from Chinese application 201180051770.3 issued on Jan. 7, 2015 (26 pages).
International Preliminary Report on Patentability from PCT application PCT/US2012/057943 issued on Apr. 10, 2014 (7 pages).
International Preliminary Report on Patentability from PCT application PCT/US2011/049383 issued on Mar. 14, 2013 (9 pages).
International Search Report and Written Opinion from PCT application PCT/US2011/049383 issued Dec. 29, 2011 (7 pages).
International Preliminary Report on Patentability from PCT application PCT/US2010/025588 issued on Aug. 30, 2011 (8 pages).
Response to Australian Office action filed on Aug. 1, 2014 for Australian application No. 2010217803 (48 pages).
Examination Report from Australian application No. 2010217803 issued on Sep. 1, 2014 (7 pages).
Batty, M. et al.,"Early processing of the six basic facial emotional expressions", Cognitive Brain Research, 2003, vol. 17, pp. 613-620.

(56) References Cited

OTHER PUBLICATIONS

Communication for EP application No. 10746912.4 issued Sep. 27, 2013 (1 page).
Response to extended European Search Report for EP application No. 10746912.4 filed on Apr. 7, 2014 (10 pages).
Office action from Chinese application 201180051770.3 issued on Jan. 7, 2015 (11 pages).
European communication for EP application 11822401.3 issued on Apr. 25, 2013 (2 pages).
International Preliminary Report on Patentability from PCT application PCT/US2013/070966 issued on Jun. 4, 2015 (7 pages).
Batty, Magali, et al., "Early processing of the six basic facial emotional expressions", Cognitive Brain Research 17, pp. 613-620, May 22, 2003 (8 pages).
Response to Examination report issued on Sep. 12, 2013 in Canadian Application 2753872, filed on Mar. 12, 2014 (24 pages).
Examination Report from Canadian Application 2753872 issued Mar. 12, 2015 (4 pages).
Voluntary Amendment filed in Australian Application 2011296331 on Mar. 12, 2013 (13 pages).
Examination Report from European Application 11822401.3 issued on Apr. 17, 2015 (3 pages).
European Communication from European Application 11822401.3 issued on May 4, 2015 (6 pages).
Office action with English translation issued in Russian application No. 2013114331 issued on Aug. 14, 2015 (12 pages).
U.S. Appl. No. 13/683,729, filed Nov. 21, 2012.
U.S. Appl. No. 61/156,239, filed Feb. 27, 2009.
U.S. Appl. No. 12/872,531, filed Aug. 31, 2010.
U.S. Appl. No. 13/249,968, filed Sep. 30, 2011.
Office Action in Australian Application No. 2015200472, issued Mar. 2, 2016, (5 pages).
European Communication from European Application 10746912.4 issued on May 31, 2016 (6 pages).
Office Action in Australian Application No. 2015200496, issued Mar. 8, 2016 (3 pages).
Chinese Office action with English translation from Chinese application 201180051770.3, dated Oct. 20, 2015, (19 pages).
Russian Decision on Grant for Application No. 2013114331/08(021174) Jun. 3, 2016 (16 pages).

* cited by examiner

METHODS AND SYSTEMS FOR ASSESSING PSYCHOLOGICAL CHARACTERISTICS

RELATED APPLICATIONS

This application claims priority under 35 U.S.C. §119(e) to U.S. Provisional Application Ser. No. 61/156,236, entitled "SYSTEM AND METHOD FOR ASSESSING AN EMOTIONAL STATE OF A SUBJECT," filed on Feb. 27, 2009, which is herein incorporated by reference in its entirety.

BACKGROUND OF INVENTION

1. Field of Invention

The present disclosure relates to psychological tests, and more particularly to systems and methods for eliciting and assessing the psychological characteristics of a test subject in relation to a research topic.

2. Discussion of Related Art

Many psychological tests exist which elicit and assess the reactions or responses of a person as they are exposed to stimuli. Such techniques typically involve, for example, presenting one or more images as stimuli to a test subject within the context of a particular topic of interest to the researcher. In response, the subject provides feedback indicative of their emotional state as he or she reacts to viewing the images. This feedback is then analyzed according to one or more emotional or motivational theories to assess the psychological characteristics of the subject as they pertain to the topic.

SUMMARY

A method and system for eliciting and assessing an emotional response from a test subject is described herein. In one embodiment, images are presented to the test subject in a rapid exposure sequence. In response to presenting the images, one or more emotional responses may be received from the test subject. A quantitative emotional profile of the test subject may be determined based on the emotional responses.

According to an embodiment, it is appreciated that an individual, when presented with a sensory stimulus (e.g., a visual stimulus), has an initial emotional reaction to that stimulus before cognitive, intellectual processing (other than simple recognition) of the stimulus begins. These initial reactions are representative of the individual's dominant emotional characteristics.

According to an embodiment, it is appreciated that the deepest, least conscious layers of thought and emotion are powerful motive forces. Through the use of the disclosed methods and systems, the dominant emotional characteristics of a person may be elicited and revealed. Once obtained, these characteristics may then be to assessed against a motivational theory to provide insight into that individual's motives, aspirations and goals. The results may be useful for a number of purposes, including but not limited to market research, performance management, and psychological evaluation.

According to an embodiment, it is appreciated that one disadvantage of prior techniques in psychological testing is that they do not account for a person's tendency to evaluate or self-censor their own emotions prior to providing the feedback. More particularly, it is appreciated that if a test subject is given enough time to react or respond after exposure to the stimulus, the subject may be reluctant or unable to voice their "impulsive" or unconscious emotional responses to the stimuli, or may instead provide a processed response rather than one reflecting "pure" emotional content. For example, the subject may reply with what they perceive as the expected or "proper" response out of a concern that their initial reaction might be incorrect, embarrassing or too revealing of their true motive. Such processed responses may also reflect the social, moral or religious norms adopted by the subject. Additionally, some psychological research has shown that conscious processing of a stimulus may mask a person's true underlying emotional state, effectively inhibiting the ability to elicit such emotional content. Accordingly, the least conscious embodiments of thought and emotion are difficult to assess using traditional techniques. As a result, the feedback garnered using these techniques may cause the psychological assessments to be skewed, rendering them less useful or reliable for their intended purposes.

In one embodiment, a test subject may be introduced to a research topic to provide a context for a psychological test. The test subject may be exposed to a series of abstract, non-verbal stimuli in rapid succession. For example, visual stimuli (e.g., images) may be used. Each of the stimuli evokes an emotion that may be linked to a core human motivation, or may be associated with a motivation through testing. As the subject is exposed to the stimuli (e.g., through a computer-based testing system), he or she may provide a response by quickly selecting the stimuli that he or she associates with their emotional state in relation to the research topic. This rapid forced selection only allows the subject enough mental processing time to recognize to each stimulus as the stimulus is presented and to form an initial emotional response to the stimulus before a response is required. A rapid stimulus-response sequence elicits a true emotional characteristic that is unencumbered by associative thinking, lying, posturing, designs or plans of the subject.

According to an embodiment, a quantitative emotional profile (also referred to as a quantitative emotional measurement) may be determined based on the responses of the test subject, which may indicate one or more emotional characteristics are present in the subject. The emotional characteristics elicited from an individual may be analyzed according to a developmental model of motivation to better understand that individual's aspirations and goals. It is appreciated that existing motivational theories do not provide a systematic and predictable method for applying the insight gained by psychological research across a group or class of people, which limits the usefulness of the emotional and motivational assessments. According to an embodiment, in the model, a set of motivational forces may be represented by a matrix where human aspirations are characterized in multiple dimensions. The model may describe, for example, how each of the motives is related to one another, how they interact with one another, the means for fulfilling each motive, and the resultant effect of fulfillment on an individual. Emotions associated with the stimuli may be validated and classified according to the model. In this manner, the reactions of a test subject to certain stimuli provide a reliable indication that a particular emotional characteristic, and corresponding motive, are present in that individual.

The results may then be used, for example, to provide insight and understanding of how people behave in, and interact with, their environment. Such insight and understanding may then further be used to assess the presence of pre-existing biases and beliefs; to provide feedback during design studies or market research; to assess the positive and negative reactions of a test subject or subjects to viewing a particular design, concept, or other stimulus; and to facilitate collaboration among a group of people in expressing their opinion about a particular topic or idea.

According to one embodiment, a method for assessing an emotional response from a test subject comprises presenting, for a first predetermined period of time, a to plurality of stimuli to the test subject through a first computer implemented interface, in response to presenting at least one of the plurality of stimuli, receiving, within a second predetermined period of time, at least one emotional response from the test subject through a second computer implemented interface, and determining a quantitative emotional profile of the test subject based on the at least one emotional response.

The plurality of stimuli may comprise a set of images, sounds, colors, smells, or textures.

The first predetermined period of time may be between approximately 500 milliseconds and approximately 1000 milliseconds. The second predetermined period of time may be equivalent to the first predetermined period of time immediately followed by a grace period, the grace period being up to approximately 250 milliseconds.

Each of the plurality of stimuli may be associated with at least one of a plurality of emotional characteristics.

The method may further comprise providing, to the test subject, at least one prompt related to a research topic. The prompt may include a matter at hand or a stem sentence.

The method may further comprise loading a stimulus set including the plurality of stimuli. The method may further comprise recording the at least one emotional response. The method may further comprise recording a test subject reaction time for each of the at least one emotional response.

Determining the quantitative emotional profile may be further based on the test subject reaction time for each of the emotional responses. Determining the quantitative emotional profile may be further based on a number of stimuli selected by the test subject. Determining the quantitative emotional profile may be further based on a type of stimuli selected by the test subject. Determining the quantitative emotional profile may further comprise comparing the at least one emotional response to at least one other emotional response.

The method may further comprise presenting, to the test subject, each of the stimuli selected by the test subject in a rapid exposure sequence, and measuring at to least one biometric response of the test subject.

The method may further comprise developing a marketing campaign based on the quantitative emotional profile, developing a consumer product based on the quantitative emotional profile, developing one or more work teams based on the quantitative emotional profile, developing a fraud management strategy based on the quantitative emotional profile, developing a therapeutic treatment strategy based on the quantitative emotional profile, classifying an advertisement based on the quantitative emotional profile, or developing a political campaign strategy based on the quantitative emotional profile.

According to another embodiment, a computer readable medium comprising computer-executable instructions that when executed on a processor performs the method for assessing an emotional response from a test subject, described above.

According to another embodiment, a method for assessing an emotional response from a test subject comprises selecting an emotion from a set of emotions based on a quantitative emotional profile of the test subject, providing, to the test subject, at least one prompt relating to a topic, presenting, to the test subject via a computer implemented interface, at least two descriptor words associated with the emotion, recording a test subject response including one of the at least two descriptor words selected by the test subject, repeating the presenting and recording acts for a plurality of descriptor words associated with the emotion, and refining the quantitative emotional profile of the test subject based on the test subject response.

According to another embodiment, a method for assessing an emotional response from a test subject comprises providing, to the test subject, at least one prompt relating to a topic, presenting, to the test subject via a computer implemented interface, a plurality of stimuli and at least two strength level selections, the stimulus classified by an emotion, recording at least one test subject response including one of the strength level selections selected by the test subject, repeating the presenting and recording acts for each of the stimuli, and determining a deviation between the strength level selection and an average strength to assess a quantitative emotional profile of the test subject based on the test subject responses, wherein the stimuli to includes at least one of a video and a speech.

According to another embodiment, a method for classifying a plurality of stimuli by one or more emotional characteristics comprises creating a matrix having a plurality of elements, assigning each of the emotional characteristics to a unique element among the elements, initially classifying each of the stimuli into at least one of the elements, presenting, to a test subject via a computer implemented interface, one of the stimuli and a prompt, recording a test subject classification of one of the stimuli into one of the elements, repeating the presenting and recording acts for each of the stimuli, and identifying, for each of the stimuli, one or more emotional characteristics where the test subject classification is the same as the initial classification.

The stimuli may comprise a set of images, sounds, colors, smells, or textures.

According to another embodiment, a method for assessing an emotional characteristic of a group of test subjects comprises presenting, to the group of test subjects via a computer implemented interface, one stimulus from a plurality of stimuli, in response to each of the group of test subjects reacting to the one stimulus, recording a test subject response including a test subject selection and a test subject reaction time, the test subject selection representing the one stimulus, repeating the presenting and recording acts for each of the plurality of stimuli, and determining which among the group of test subjects has a similar emotional characteristic based on the test subject responses.

The plurality of stimuli may comprise a set of images, sounds, colors, smells, or textures.

The method may further comprise identifying at least one cluster of stimuli based on the test subject responses. The method may further comprise presenting, to one or more other test subjects, each of the stimuli in the at least one cluster of stimuli, and receiving, in response to presenting each of the stimuli, a description of a feeling evoked in each of the test subjects by each of the stimuli.

According to another embodiment, an apparatus for eliciting an emotional response from a test subject comprises a presentation component for presenting, to during the test, a plurality of stimuli, and a response component for receiving, during the test, at least one test subject selection representing the emotional response.

The apparatus may further comprise a configuration component for configuring a test. The plurality of stimuli may comprise images, sounds, colors, smells, or textures.

The apparatus may further comprise a classification component for classifying the at least one test subject selection into one element of a matrix. The apparatus may further comprise an assessment component for assessing the emotional response. The apparatus may further comprise a comparison component for comparing the emotional response of the test subject with a second emotional response of a second test subject.

According to another embodiment, a computer implemented method for assessing feedback pertaining to a topic comprises presenting, in an interface of a computer system, a plurality of visual stimuli to a test subject, in response to presenting at least one of the plurality of visual stimuli, receiving feedback from the test subject through an interface of the computer system, wherein the feedback comprises a response indicative of an emotional state of the test subject in relation to the topic, and determining an emotional quantitative measurement of the test subject based on the feedback.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
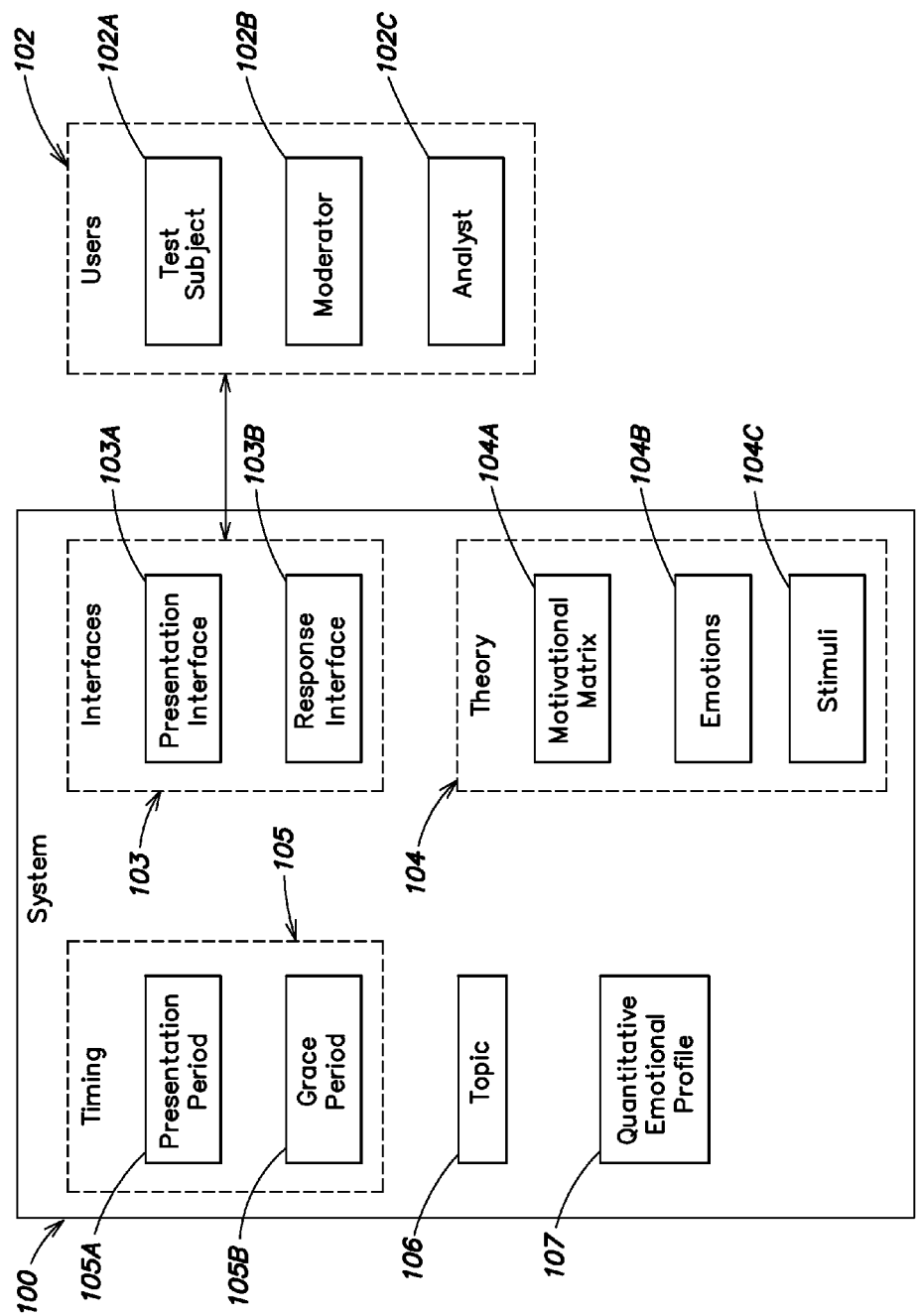
FIG. 1 illustrates an exemplary system for assessing psychological characteristics in which various embodiments of the disclosure may be implemented.

Embodiments of this invention are not limited in its application to the details of construction and the arrangement of components set forth in the following description or illustrated in the drawings. Embodiments of the invention are capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

An emotion, as used herein, is broadly defined an affective state of consciousness experienced by a person; e.g., affection, desire, fear, happiness, pride, etc. An emotional response, as used herein, is broadly defined as one or more characteristic emotive reactions by a person to one or more stimuli.

System Overview

FIG. 1 shows various interactions of a system 100 for assessing psychological characteristics according to various embodiments of the disclosure. As shown, there may be one or more types of users 102 of the system, including, but not limited to, one or more test subjects 102A, one or more moderators 102B, and one or more analysts 102C. Test subject 102A (or simply "subject"), as used herein, is broadly defined as an individual participating as an object of an experiment or test.

According to one embodiment, there may be only one test subject 102A participating in the test at any given time.

According to another embodiment, there may be multiple test subjects 102A participating in groups. In one example, responses of multiple test subjects 102A received during a test, performed in one particular context, may used to identify one or more psychological characteristics of the subjects under a "crowdsourcing" or distributed group collaboration theory. In another example, a focus group may be tested regarding a particular topic, and the results of the test may be used to validate the stimuli as to one or more associated emotional characteristics. The multiple test subjects 102A may participate at the same time or at different times, and may participate at the same location or at different locations.

Moderator 102B may be an individual who configures and/or administers the test to test subject 102A. According to various embodiments, moderator 102B may be responsible for selecting content that forms stimuli for the test, providing a context for the test, or providing other input to the test.

In another implementation, moderator 102B may provide instructions to test subject 102A, or may facilitate the test in other ways, including, for example, procuring the subject or interviewing the subject. Moderator 102B may be present to with test subject 102A at the time the test is administered, although the test may be configured such that the test subject may participate outside of the presence of the moderator.

Analyst 102C may be an individual who reviews and/or analyzes the results of the test. Analyst 102C may be the same individual as moderator 102B.

One or more users 102 interface with the system 100 through at least two interfaces 103. A presentation interface 103A may include a display for displaying visual stimuli, such as images or words to one or more users 102. Presentation interface 103A may include a graphical user interface (GUI) or any other type of interface capable of presenting stimuli to a user. Presentation interface 103A may include other types of devices for presenting stimuli that evoke emotional responses, such as audio information.

A response interface 103B may be provided that includes one or more input elements including a keyboard, mouse, button, touch screen or other input device type. In one example, the response interface 103B may be integrated into a smartphone, for example, Apple iPhone®, RIM BlackBerry®, or another device having similar capabilities. Response interface 103B may be coordinated with the presentation interface 103A, for example, as a control button displayed within the GUI. Response interface 103 may include devices to measure one or more physiologic functions of the test subject 102A, including, but not limited to, voluntary responses, involuntary responses, and biometric responses. It will be understood that the presentation interface 103A and the response interface 103B may be the same interface.

In one example implementation, a theory 104 for assessing the psychological characteristics of the test subject 102A includes a motivational matrix 104A, a plurality of emotions 104B, and a plurality of stimuli 104C. The motivational matrix 104A describes a psychological model of motives or aspirations of the test subject 102A, which various embodiments thereof will be described below. The plurality of emotions 104B includes one or more mental perceptions of the test subject 102A associated with an affective state of consciousness, various examples thereof which will be described below. The plurality of stimuli 104C includes sensory stimuli that, when presented to the test subject 102A, may elicit one or more of the emotions 104B from the test subject 102A.

In one embodiment, the motivational matrix 104A represents a psychological model describing nine core aspirations of the test subject 102A, arranged in two dimensions including a focus of aspiration versus a level of aspiration. The focus of aspiration may describe where the person is aspiring to improve their lives. For example, an intra-psychic focus describes how the person feels about oneself; an instrumental focus describes how the person feels about his/her activities; and an interpersonal focus describes how the person feels about his/her relationships with others. The level of aspirations may describe the desired emotional state of the person as he or she fulfills their aspirations. For example, "establishing potential" describes how a person feels when he/she believes that he/she possesses the ability to pursue his/her aspiration; "experiencing process" describes how a person feels when he/she is successfully progressing toward his/her aspiration; and "creating product" describes how a person feels when he/she has achieved his/her aspiration.

Figure 2:
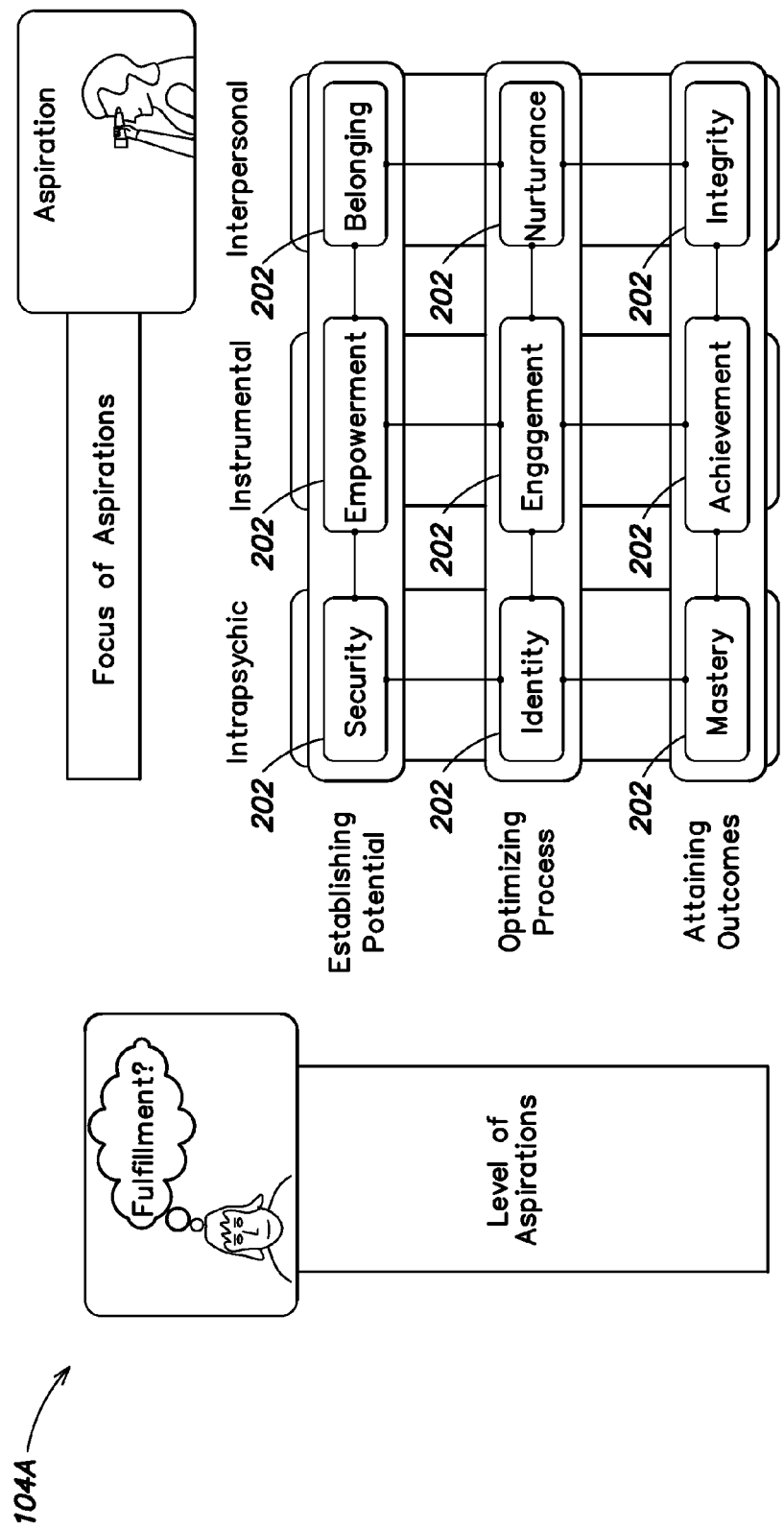
FIG. 2 illustrates an exemplary motivational matrix in accordance with one to embodiment of the disclosure.

FIG. 2 illustrates an exemplary motivational matrix 104A consistent with one embodiment. The motivational matrix 104A includes nine motives 202, each motive 202 representing a combination of each focus of aspiration and level of aspiration, as described above, including security, identity, mastery, empowerment, engagement, achievement, belonging, nurturance, and integrity. In one example, "security" describes how a person feels when aspiring to establish potential within oneself. In another example, "achievement" describes how the person feels when aspiring to create a product through his/her activities. It will be understood that the motivational matrix 104A described herein is exemplary and that other motivational matrices may be developed to describe alternative psychological models.

Figure 3:
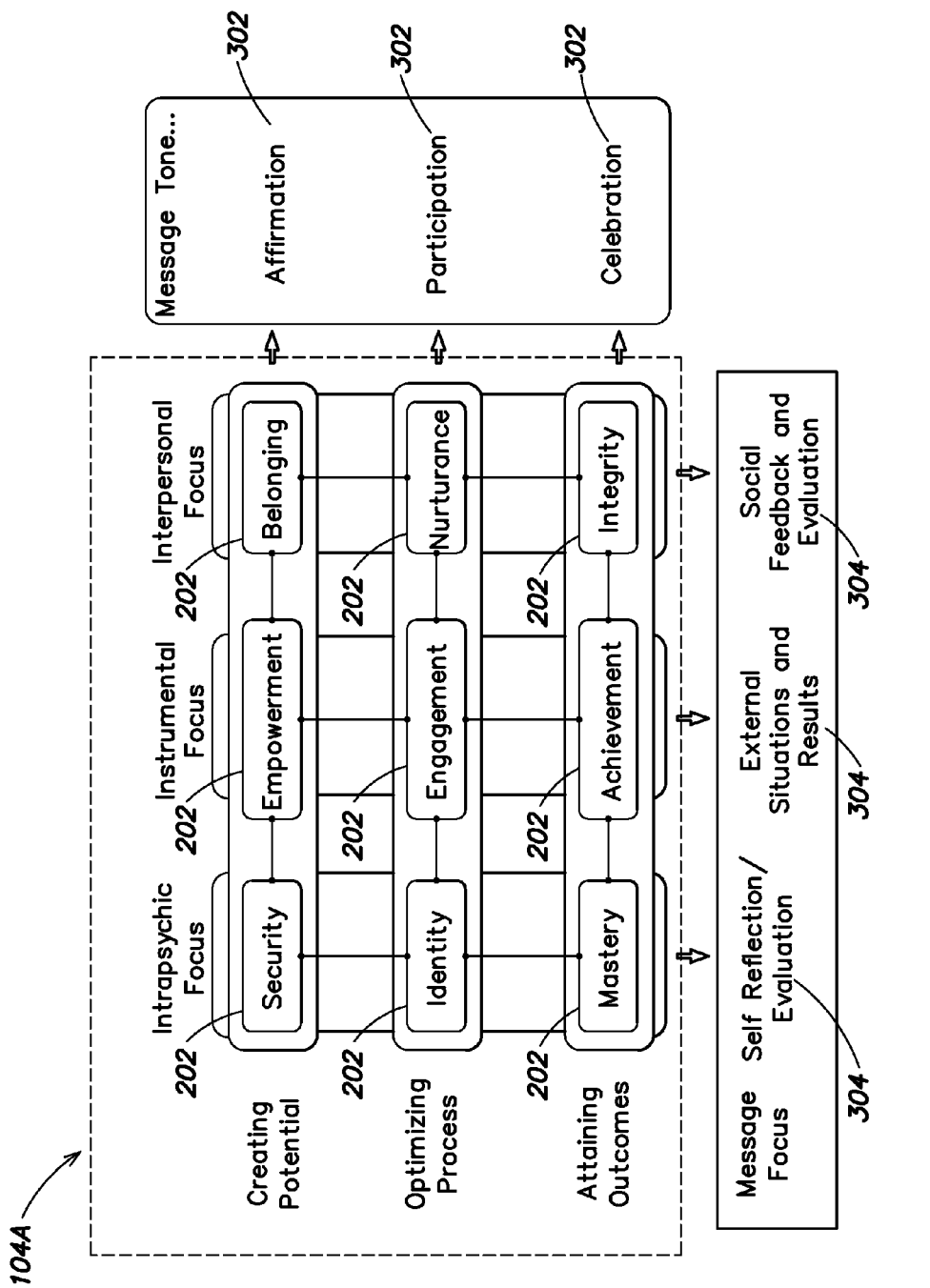
FIG. 3 illustrates an exemplary motivational matrix in accordance with one embodiment of the disclosure.

According to another embodiment, illustrated in FIG. 3, the motivational matrix 104A may be used to interpret the underlying motives 202 of the test subject and apply those interpretations. For example, a test subject having a motive of "engagement" may have a positive response a message having a participatory tone 302 and a focus 304 on attaining results. Messages, such as those for marketing a to consumer product, may then be developed using this information, which may appeal to individuals having a similar motive.

According to various embodiments, each of the motives or aspirations described by the psychological model represent one or more emotions 104B experienced by the test subject 102A when the test subject 102A possesses the corresponding motive or aspiration and is exposed to an evocative stimulus 104C. For example, the emotions 104B may include feeling brilliant, superior, visionary, experienced, dominant, or excellent. Each of these emotions may, according to the model, be associated with the motive of mastery, as described above. Accordingly, when the test subject 102A possesses the motive of mastery, he/she is likely to experience one or more of the above emotions in response to certain stimuli 104C.

In various embodiments, the stimuli 104C may include, but are not limited to, images, sounds, smells, and other forms of sensory stimuli. Exemplary stimuli include images such as a person fastening an automotive seat belt, a fingerprint, a surgeon performing surgery, an airplane taking off, several business professionals working together, an athlete wearing a medal, children playing together, a mother tending to a sick child, and a military officer being decorated with ribbons.

The stimuli 104C may be classified by a type of stimuli. For example, images containing the color red may be classified as such. Any characterization of the type may be used, depending on the nature or character of stimuli being classified.

Each of the stimuli 104C may be associated with one emotion 104B, the emotion in turn corresponding to one motive in the motivational matrix 104A. For example: a person fastening an automotive seat belt evokes a feeling of security, a fingerprint (identity), a surgeon performing surgery (mastery), an airplane taking off (empowerment), several business professionals working together (engagement), an athlete wearing a medal (achievement), children playing together (belonging), a mother tending to a sick child (nurturance), and a military officer being decorated with ribbons (esteem). Accordingly, one of the stimuli 104C presented to a test subject 102A possessing one of the motives will elicit the emotion corresponding to the motive.

According to one embodiment, user 102 interaction with a test system (e.g., system 100) may be subject to certain timing attributes 105. For instance, one or more timing attributes 105 may control how long certain stimuli are presented to the user, and how responses should be, for example, received, validated, classified, and interpreted. In one embodiment, presentation period 105A may be defined that describes an amount of time a test subject (e.g., test subject 102A) is exposed to certain stimuli 104C through a presentation interface 103A. The amount of time may be determined based on a test theory. For example, one stimulus 104A may be presented to the test subject long enough for simple recognition of the stimulus to occur, but not so long that the test subject begins cognitive processing of the stimulus. In one embodiment, presentation period 105A may be between approximately 500 and approximately 1000 milliseconds.

According to one embodiment, test subject 102A may respond through the response interface 103B during presentation period 105A. A grace period 105B may also be defined that describes an amount of time a test subject may respond through response interface 103B after presentation period 105A has expired. Test subject 102A may be further exposed to the stimuli or a portion of the stimuli for at least a portion of the grace period 105B. For example, the grace period 105B may immediately follow the presentation period 105A and be up to approximately 250 milliseconds. Shorter or longer periods may be used that are also effective.

In one example implementation a topic 106 may be provided that indicates to the test subject a context for the test. For example, a topic may include a question regarding a particular subject matter, such as "How do you feel about (the particular topic)?" In another embodiment, a response to this question may be obtained by having the subject complete a sentence, such as "I wish I could feel more _____ about (the particular topic). The subject may, for example, perform sentence completions by selecting stimuli that evoke feelings that would be appropriate to fill the blank in the sentence. In one embodiment, topic 106 may be provided to the test subject 102A by the moderator 102B. In another embodiment, topic 106 may be provided to the test subject 102A through the presentation interface 103. In another embodiment, topic 106 may be provided to the analyst 102C by the moderator 102B, or vice versa.

As will be discussed in further detail below, the system 100 may generate a quantitative emotional profile 107. In one embodiment, the quantitative emotional profile 107 may be a quantitative measure of the emotional or motivational characteristics of the test subject 102A, including, for example, the emotion 104B experienced by the subject 102A and a strength of the emotion 104B.

Example Process for Assessing an Emotional Response

Figure 4:
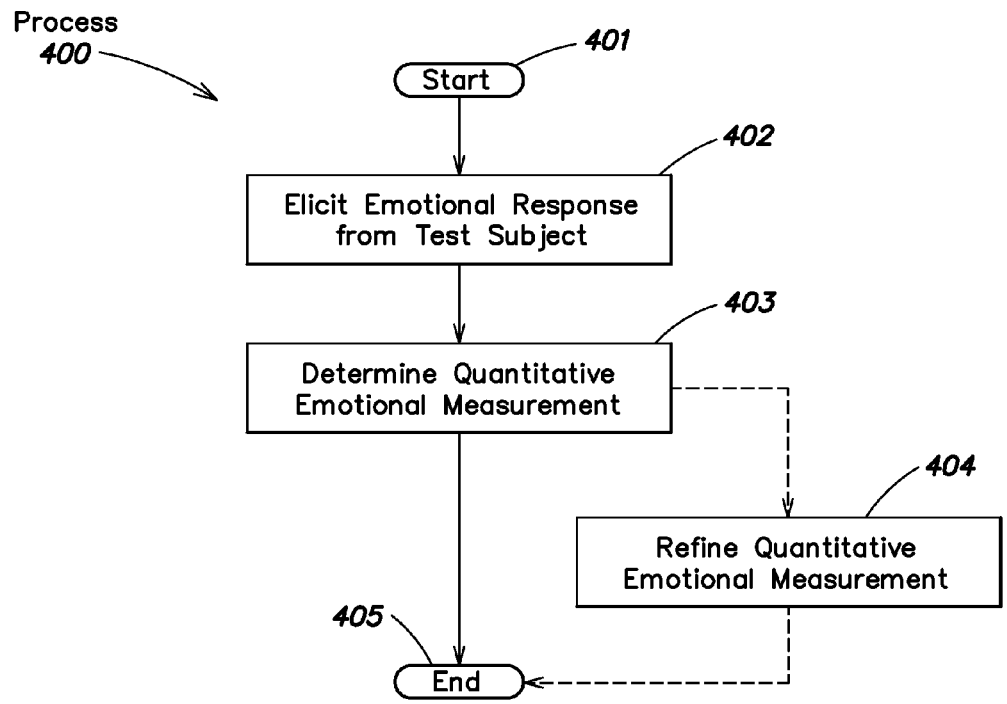
FIG. 4 illustrates an exemplary process for eliciting and assessing an emotional response from a test subject in accordance with one embodiment of the disclosure.

FIG. 4 illustrates a process 400 for assessing an emotional response from a test subject according to one embodiment. Process 400 may be performed, for example, by the system 100 as discussed above with reference to FIG. 1. In one embodiment, process 400 includes eliciting an emotional response from the test subject and determining a quantitative emotional profile of the test subject based on the emotional response. Process 400 may optionally include refining the emotional quantitative profile of the test subject, for example, by subjecting the subject to further testing, questioning, or interviewing.

At block 401, process 400 starts. At block 402, an emotional response is elicited from a test subject, as will be described below with reference to FIG. 5. For example, act 402 may include establishing, in the mind of the test subject, a research topic to be considered while taking the test, such as a "matter at hand." Act 402 may further include providing, to the test subject, a directed inquiry, such as a "stem sentence." In one example, the research topic may be established by telling the subject that they will be "completing a sentence with a picture" and introducing the "stem sentence," for example, "I wish I could do my laundry in a way that made me feel more _____."

Additionally, act 402 may further include performing a stimulus test. The stimulus test may include, for example, presenting a series of visual stimuli in a rapid exposure sequence to the test subject through a computer implemented interface, as will be described below with reference to FIG. 6. One or more of the stimuli may provoke an initial emotional reaction in the test subject. In response to presenting one or more of the stimuli, feedback may be received from the test subject (e.g., through one or more interfaces), where the feedback includes a response indicative of the emotional state of the test subject in relation to the research topic. The feedback and a corresponding response time for each response may be recorded (e.g., by system 100) for analysis.

In one embodiment, act 402 may include performing, prior to the stimulus test described above, a "dial" or strength test, where the subject may be exposed to one or more stimuli (e.g., a video, advertisement, or speech) and asked to rate the strength of their feelings with respect to the stimuli on a scale of two or more strength values. The subject may then be asked to complete a sentence, using the stimulus test described above. One exemplary sentence is "The reason I was very positive about this part [of the video or speech] is because it made me feel _____."

At block 403, a quantitative emotional profile of the test subject based on the feedback is determined. In various embodiments, the quantitative emotional profile represents the dominant emotional characteristics of the test subject, and the relative strengths of these characteristics, as elicited in act 402. If the stimuli selected by the test subject in act 402 have been previously associated with a particular emotion, the response and response time may indicate the presence and strength of the emotion in the test subject, where shorter response times indicate higher strength. Subsequently, the emotion represented by the selected stimuli, which may be classified according to the motivational matrix, may indicate the presence of the corresponding core motive. For example, if, among all the stimuli selected by the test subject, the majority of selected stimuli are classified into the motive of security, then the presence of the security motive in the test subject may be inferred.

After all images in the set have been presented, the resulting responses are tabulated and analyzed. Because each image is known to elicit a particular emotional characteristic, the dominant emotional characteristic of the test subject may be determined by analyzing the number of images selected having one particular emotional characteristic and the response time for each of those selected images. For example, if 45 images are presented, arranged in five cycles of nine images each, each of the nine emotional characteristics is represented by five different images. If the subject chooses more images representing one emotional characteristic than any other, and/or the subject chooses images representing one emotional characteristic more to quickly than images representing other emotional characteristics, the subject is likely to harbor the one emotional characteristic as the dominant characteristic.

In another embodiment, the responses are used as a quality score or weighting that determines the nature (salience, strength, or quality) of the emotional response by the test subject. The weighting may be based on the number of responses received respective to a particular element of the motive matrix, or according to the respective response time. For example, responses having shorter than average response time may be given more weight than those having longer than average response time. Accordingly, responses having greater weight are likely to indicate that the subject harbors the emotional characteristic associated with the respective stimulus as the dominant characteristic. In another embodiment, this response time may be compared to response times for other stimuli, or for the same stimulus in other presentation conditions, to develop a score or weighting indicative of the quality of the response to the stimulus.

Optionally, at block 404, the quantitative emotional profile may be refined. For example, the test subject may be subjected to additional interviews and/or testing, including, but not limited to, a "linguistic expansion" test. The results of this refinement may be used to further assess the subject's emotional response according to the motivational model.

At block 405, the process 400 ends.

Example Process for Eliciting an Emotional Response

Figure 5:
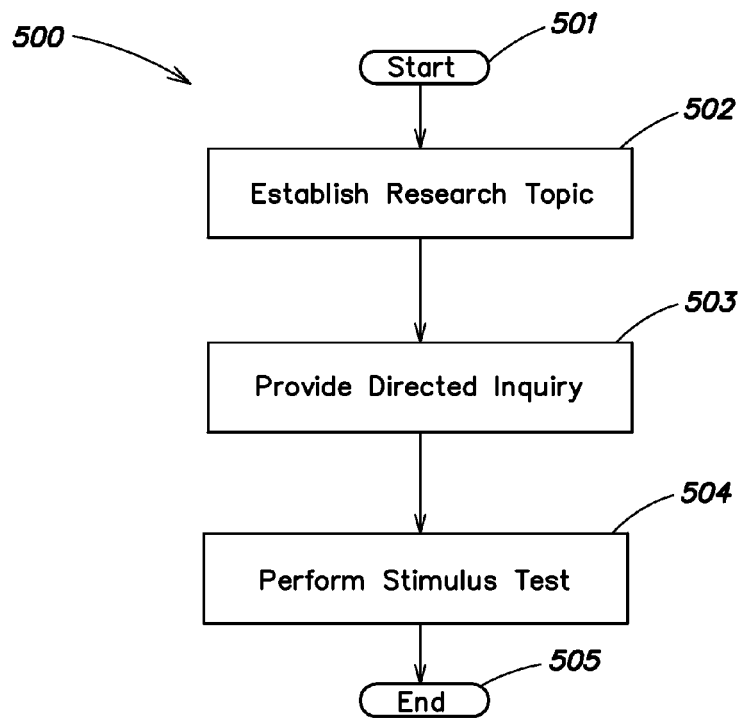
FIG. 5 illustrates an exemplary process for eliciting an emotional response from a test subject in accordance with one embodiment of the disclosure.

FIG. 5 illustrates a process 500 for eliciting an emotional response from a test subject according to one embodiment. Process 500 may be performed, for example, by the system 100 as discussed above with reference to FIG. 1. Process 500 starts at block 501.

At block 502, a research topic is established. The research topic may include any subject matter of interest to a researcher. For example, the research topic may include, but is not limited to, a consumer product or service, a retail establishment, a community, a job, a task, a leisure activity, or a political campaign. It will be understood that the research topic may include any subject matter, and more particularly, may further be directed toward ascertaining any subjective feelings that the subject may have towards the subject matter. The research topic may, for example, in the context of dishwashing liquid, direct the subject to consider the effectiveness, scent, color, toxicity, or other relevant characteristic of the dishwashing liquid.

Act 502 may include providing, to the subject, one or more prompts in a manner that communicates the research topic to the subject. For example, the subject is asked to consider a "matter at hand." The matter at hand provides a context for the test, and includes the subject matter for which the emotional state of the subject is to be elicited. The inquiry may be an incomplete sentence in the form of "Thinking about (a particular topic) makes me feel _____." For example, "Thinking about air fresheners makes me feel _____."

At block 503, the subject may be provided with a second prompt to direct them to a specific emotional target within the matter at hand, for example, a stem sentence. The subject may be instructed to select stimuli that he or she most closely associates with the emotion completing the stem sentence. The stem sentence may be, for example, a "fill-in-the-blank" type prompt in the form of "When I use (a particular topic) I am trying to make myself feel more (or less) _____." For example, the subject may complete the stem sentence by thinking, "I wish there was an air freshener that would make me feel more relaxed." Subsequently, if the subject is exposed to a stimulus that he or she associates with relaxation, he or she may select that stimulus in response.

In another embodiment, the subject may be presented with a "fill-in-the-blank" type of prompt in the form of "When I use (a particular topic) I am trying to make myself feel more/less _____." The subject may be presented with two sets of stimuli (e.g., images), one set representing positive stimuli evoking a positive response, and one set representing negative stimuli evoking a negative emotional response, and instructed to choose those stimuli that evoke emotions that are stronger ("more") or weaker ("less") in accordance with the prompt.

After establishing the research topic, at block 504, a stimulus test is performed on the test subject, one embodiment of which is described below with reference to FIG. 6. At block 505, the process 500 ends.

Example Process for Performing a Stimulus Test

Figure 6:
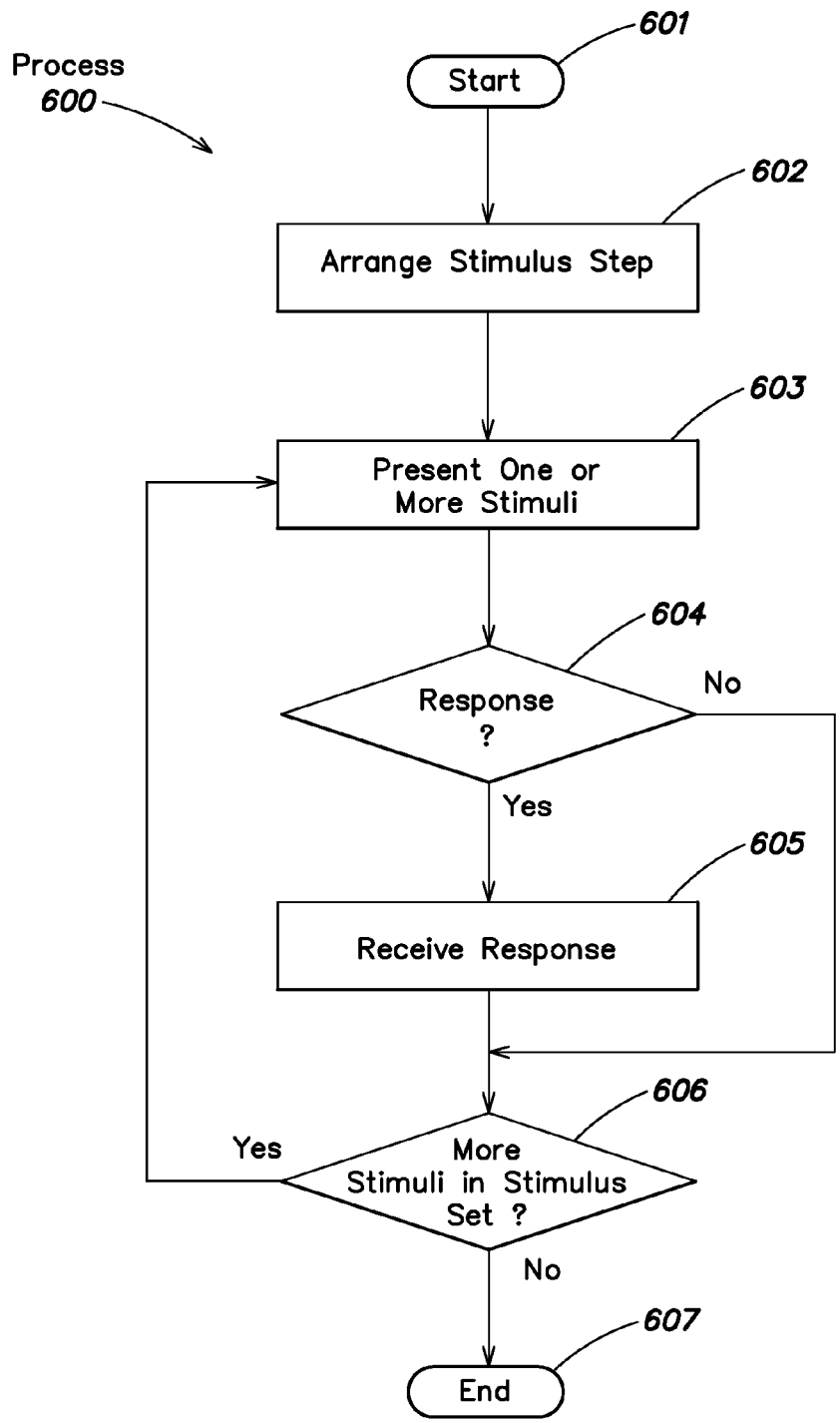
FIG. 6 illustrates an exemplary process for performing a stimulus test according to one embodiment of the disclosure.

FIG. 6 illustrates a process 600 for performing a stimulus test according to one embodiment. At block 601, the process 600 starts. At block 602, a stimulus set including non-verbal stimuli is arranged. The stimuli may be images. However, a non-exclusive list of non-verbal stimuli in the stimulus set includes images, sounds, colors, smells, and the like. According to one embodiment, it is appreciated that one disadvantage of prior techniques is that they are not consistently able to provide access to thoughts and feelings that may be below the threshold of subjects' conscious awareness. It has been established in some psychological research that areas of the brain responsible for emotional reactions and emotional memories are distinct from areas of the brain responsible for conscious thought. It has also been established that images can perform a projective or enabling function, allowing research respondents to gain access to emotions or ideas that are below the threshold of consciousness, or allowing respondents to articulate feelings or thoughts that they might otherwise be unable to articulate.

Figure 7:
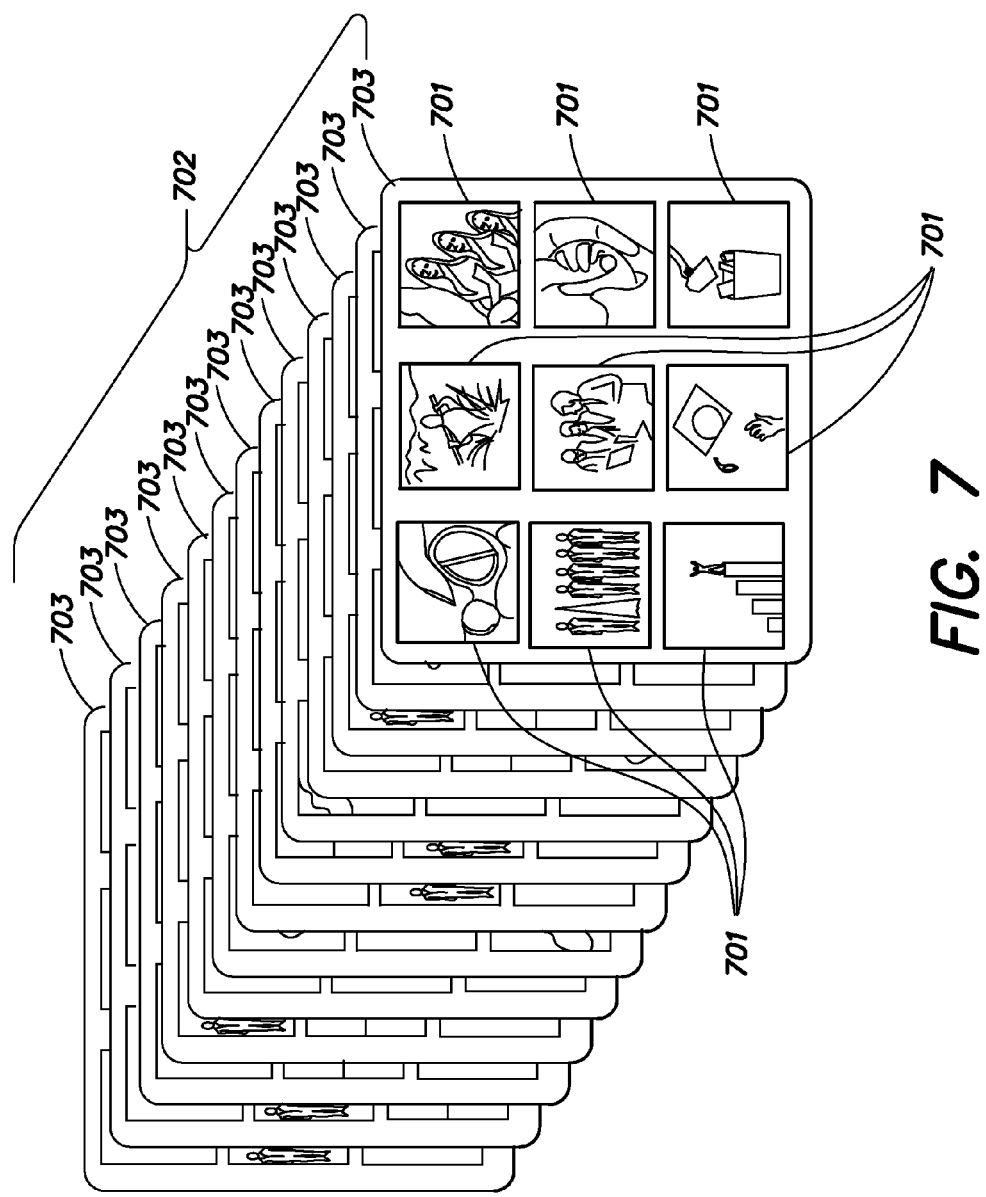
FIG. 7 illustrates an exemplary stimulus set in accordance with one embodiment of the disclosure.

An exemplary stimulus set is shown in FIG. 7. Each image 701 is known to elicit a particular emotional characteristic from an individual. Each image 701 may be classified, for example, according to a motivational model comprising a matrix of motives, or may be used for raw comparisons between different test subjects. The matrix may contain a plurality of elements, each representing a different motive. For example, a non-limiting matrix of motives 104A, as shown in FIG. 2, may include security, empowerment, belonging, identity, engagement, nurturance, mastery, achievement, and integrity, arranged by focus of aspiration versus level of aspiration. Thus, each image 701 in the set may be associated with one of the motives in the matrix represented by the model. Classification of images 701 may occur before the test begins, or the images may be classified dynamically as the test proceeds. For example, images which have strong quantitatively validated emotional associations with each of the motives may be used. When these images are selected by the test subject, the images reliably indicate the presence of the associated motive in the test subject. In another example, images may be classified into a pre-selected matrix of motives and validated through testing. In yet another example, images selected most often by a group of test subjects in a similar context (e.g., using a crowdsourcing approach) may be classified into one or more emotional states or motives based on the context.

In one embodiment, as shown in FIG. 2, the matrix 104A may comprise nine elements; however, it will be understood that the number of elements in the matrix may vary according to the particular motivational model being utilized for the research. The image set 702 comprises at least one image for each element in the matrix. For example, in a matrix having nine elements, the image set 702 contains at least nine images. In one embodiment, each element of the matrix is represented by an equivalent number of images 701 in the set; for example, in a matrix having nine elements, the image set 702 may contain nine, 18, 27, 36, 45, or higher multiples of nine images. In this manner, the subject is given multiple opportunities to respond to images eliciting the emotion that the subject is experiencing, and the results of the test are improved. Each image may be included in the set once.

According to one embodiment, it is appreciated that a reaction by the test subject to the presentation of a visual stimulus includes the evocation of an emotional response to the stimulus before extensive cognitive processing (other than simple recognition) of the stimulus begins. In one embodiment, this period of "pre-cognitive" processing has been observed to be approximately 500 milliseconds to one second in length. Insights about psychological processing time and psychological processing sequence may be leveraged to develop a range of diagnostic procedures that carefully controls a total time of stimulus exposure before a response from a subject, and thus eliminates or strictly limits time for conscious processing before a response is made. The diagnostic procedures include tests having very short stimulus exposures (less than approximately one second), as well as tests with longer periods of exposure, which may be used separately and in combination as part of a diagnostic assessment.

Referring again to FIG. 6, at block 603, the subject is presented with a series of stimuli in rapid succession. In one embodiment, images 701 are presented through a computer implemented interface, such as a display. For example, each image 701 in the image set 702 may be presented, during a test, to the test subject in a random order to avoid enabling a test subject to predict a particular sequence through familiarity gained during testing.

In one embodiment, each image 701 in the image set 702 is presented once during the process 600. One "cycle" of images 703 includes one image 701 for each element of the motive matrix. If the image set 702 contains more than one image 701 for each element of the motive matrix, then one cycle of images 703 may be presented before the next cycle 703 begins; however, the order of images 701 presented within each cycle 703 may be random.

At block 604, if exposure to any stimulus in the series provokes an emotional response that the subject associates with the topic, the subject is forced to quickly indicate this by selecting the stimulus during the presentation period or within a short time thereafter referred to as the grace period. The subject indicates his or her selection, or emotional response, to each stimulus in the series through a second computer interface, which may include a button, keyboard, mouse, or other such device. Responses from the test subject may be received in the form of a positive or negative response to each image. A positive response may be, for example, one in which the test subject responds favorably to viewing the image, or one in which the test subject has a significant or strong emotional association with the image. A negative response may be one in which the test subject responds unfavorably to viewing the image, or one in which the test subject has little or no emotional association with the image.

The responses may include one or more values representing the strength or quality of the test subject's emotional state as elicited by each image. For example, the test subject may quantify his or her emotional state as being strong, moderate, or weak. The list of responses may include one or more values representing one or more behaviors (e.g., a button press or a screen touch) it may also include one or more of these behaviors in association with one or more physiologic states in relation to each image, such as (but not limited to) brain blood flow, resistance, temperature, motion, audible measurement, and heart rate.

At block 605, a response to each of the stimuli may be received and recorded along with a reaction time. The resulting data may be tabulated and analyzed by a software program that characterizes a dominant emotional state of the subject. Biometric feedback, including pulse, blood pressure, eye movement, and the like, may also be collected from the subject.

At block 606, if there are stimuli in the set that have not yet been presented, the process 600 returns to block 603. Otherwise, process 600 ends at block 607.

According to another embodiment, each of the stimuli selected by the test subject during process 600 may be presented again to the subject in rapid succession. Biometric feedback may be collected and measured during the presentation to obtain additional information about the strength of feeling about each stimulus by the subject. The feedback may be used to refine the quantitative emotional profile of the subject.

Example Timing Sequence

Figure 8:
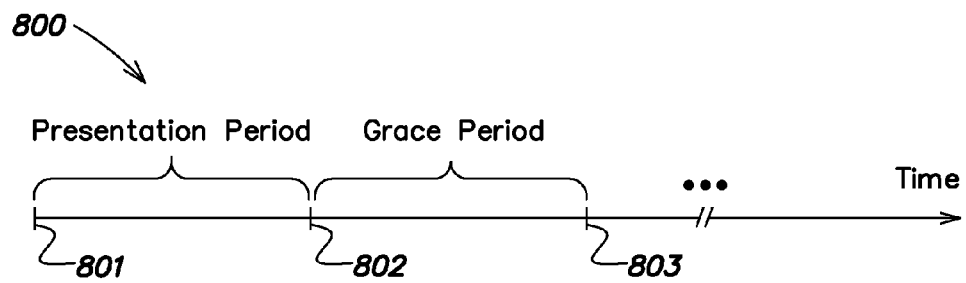
FIG. 8 illustrates an exemplary timing sequence in accordance with one embodiment of the disclosure.

FIG. 8 shows a timing sequence 800 in accordance with an embodiment of the disclosure. Starting at 801, each image is presented for approximately 500 milliseconds to 1 second (the "presentation period"). At the end of the presentation period 802, an optional "grace period" begins. During the grace period, the image may be removed immediately, or gradually, from the test subject. For example, the image may be wiped or faded from view over the course of at least a portion of the grace period. In another example, a progress bar may be displayed to indicate an amount of time remaining until the grace period ends. The grace period may be approximately zero to 250 milliseconds immediately following the presentation period. The grace period ends at 803.

In another embodiment, the visual stimulus is removed after display for a predetermined time, after which the test subject is permitted to respond. In this way, the test subject is permitted to respond after the visual stimulus is shown, but the visual stimulus is removed so that only the emotional response is measured. In another embodiment, the stimulus may be shown after a second image (to "prime" the response) or before a second image (to "mask" the impact of the stimulus).

The timing sequence 800 may repeat for each image in the image set. Shorter or longer periods may be used that are also effective.

Example Process for Receiving Test Responses

Figure 9:
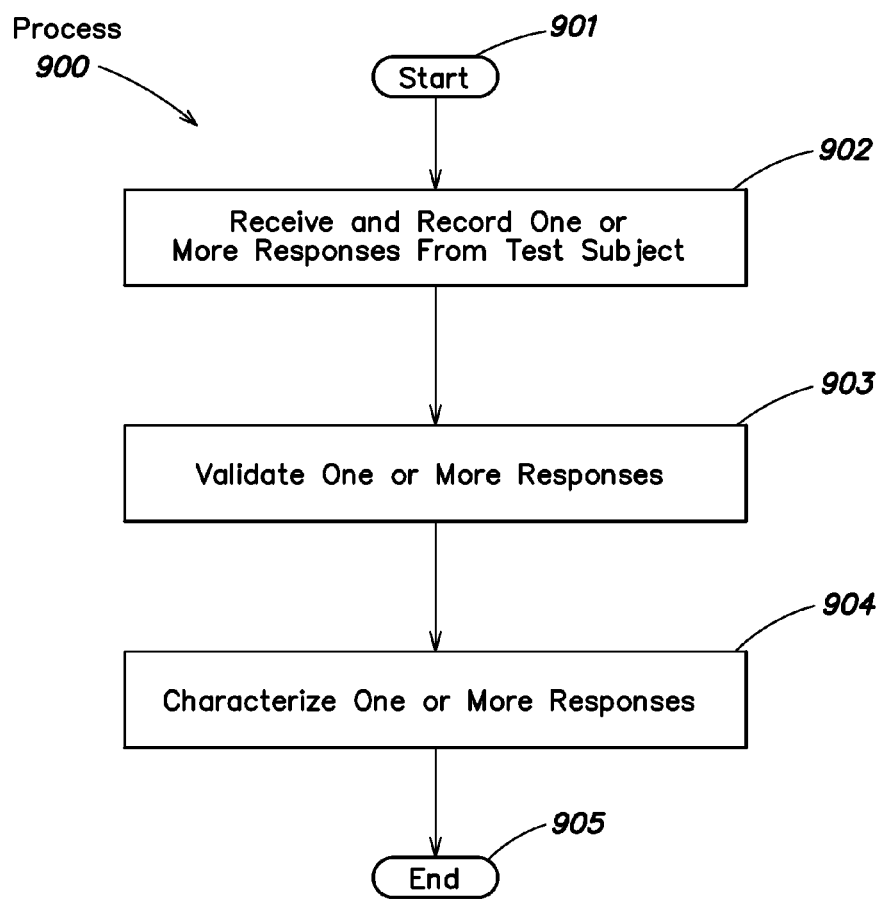
FIG. 9 illustrates an exemplary process for receiving one or more responses from a test subject in accordance with one embodiment of the disclosure.

FIG. 9 shows a process 900 for receiving one or more responses from the test subject in accordance with one embodiment of the disclosure. For example, process 900 may be implemented in accordance with process 600 as shown in FIG. 6 and discussed above. At block 901, the process begins. At block 902, the subject, via a user interface, may react or respond to each image by, for example, selecting a button (e.g., by clicking a mouse) during the presentation period or the grace period, if any. It will be understood that other methods of responding may be utilized, for example by pressing a key, touching a screen, speaking or shouting, shaking or pointing a motion-sensitive device, etc. Responses received outside of the presentation and grace periods may be invalid as to the respective stimulus. The response, if any, to each image is recorded along with a response time which is measured from the time when the image is first presented until the time when the response is received.

At block 903, the responses may be validated. If a response is received less than approximately 150 milliseconds after the stimulus is presented to the subject, it is unlikely that the subject has had an adequate amount of time to recognize and react to the stimulus in a meaningful manner. Rather, a response received in such a short amount of time may be an erroneous response, or an attempt by the test subject to subvert the test, and as such may not be useful for assessing the subject's emotional characteristics reliably. Likewise, a response received more than 300 milliseconds after the presentation period ends is likely to occur after the subject has had an opportunity to consciously process the response, and accordingly may be of marginal value in the assessment of the subject's emotional characteristics. Responses having response times in these ranges may be characterized as invalid or an attempt by the subject to subvert the test, depending on the context of the test. For example, during a job interview, the subject may have a reason to subvert the test if he or she believes that doing so might improve the chance of obtaining employment.

At block 904, the responses may be characterized. If the subject responds to none of the stimuli, there is no useful information for assessing the subject's emotional characteristics. Likewise the results of the test are likely to be skewed if the subject responds to the stimuli in a predictable pattern, for example by selecting every third image in the sequence or in a repeated pattern, selecting images randomly, selecting only images containing a certain color or object, or selecting all images in the set. It will be understood that other methods of characterizing the responses exist.

At block 905, process 900 ends.

Other Examples

Another embodiment of the method may further include comparing a quantitative emotional profile of the test subject with a quantitative emotional profile of other test subject(s). For instance, this may be useful to determine how similar an emotional state of one subject is to another subject or group of subjects. Results from the same subject at different points in time—or at different places—can be used to describe emotional changes in a subject across points in time or across different locations.

In one embodiment, large numbers of responses to large numbers of stimuli are collected and presented using any of the presentation methods described above, for example, using a crowd-sourcing approach. Statistical analysis of these responses would be used to identify "clusters" of responses within the overall dataset, indicative of predominant emotional states within the large group overall, or within subgroups of the total group. This technique could be used to describe the nature of these emotional states in detail based on the individual responses which fall into a response cluster, or on the responses which fall most closely to the statistical center of a response cluster.

In one embodiment, visual stimuli testing techniques are combined with interviews (e.g., psychological interviews, job interviews, police interrogation, etc.). Because a subject's emotional state can be assessed quickly and accurately, an interviewer may use the method prior to or in association with an interview to identify lines of questioning that the interviewer should take (e.g., if an emotion detected is fear, then asking probing questions of the subject related to fear).

In one embodiment, lists of emotional descriptor terms are presented, in a to linguistic expansion test, to the subject in a further assessment battery as a means for further defining emotions that are revealed in the visual stimulus exercise. Responses to these lists of terms can be analyzed statistically in real time to determine which of the terms are most accurate descriptors of the subject's emotional state as revealed in the image exercise. In one embodiment these terms may be presented in a forced choice exercise to obtain ranking of terms that are most descriptive of the emotional state. In another embodiment, these terms may be presented in rapid sequence with respondent choosing words that describe an emotional state indicated by images previously chosen.

Another embodiment of the method may include assigning descriptive names to each one of the visual stimuli. The method may further include comparing the positive and/or negative selections by the test subject with the descriptive names to determine the emotional state of the test subject.

Another embodiment of the method may also include classifying of emotions into a set of two or more emotion classes. Classifying the set of emotions may include creating multiple stimulus cue lists. The cue lists may be arranged into groups, where each group represents a different emotional state. One or more sets of stimuli may be presented to the subject to test for particular emotion classes. The stimulus selection patterns of the test subject may be correlated with an emotional state by indexing the stimuli selected by the test subject into the emotion classes. In one example, there may be nine sets of images, each of which sets includes an image relating to a particular emotion class. If the subject selects the images from one particular emotion class more frequently than from other emotion classes, then the subject is more likely to feel the emotional characteristic of the emotion class.

Another embodiment of the method may relate to using such visual stimuli testing methods along with interviews (e.g., psychological interviews, job interviews, police interrogation, etc.). Because a subject's emotional state can be assessed quickly and accurately, an interviewer may use the method prior to or in association with an interview to identify lines of questioning that the interviewer should take (e.g., if an emotion detected is fear, then asking probing questions of the subject related to fear).

Another embodiment of the method relates to a computer system that is capable of performing different embodiments as disclosed herein.

Classifying Stimuli

In one embodiment, stimuli may be classified according to a motivational model by presenting a list of classified stimuli comprising, for example, words, terms, phrases, images, smells, shapes, substances, textures, or colors to multiple test subjects. Each stimulus in the list has a known or hypothesized relationship with one emotion. These relationships may be vetted by experts analyzing the stimuli, or through research and testing. The test subjects may select one or more of the stimuli in the list relative to an established motive. For example, if the motive is security (of, e.g., their home), the test subjects are asked to select stimuli that elicit emotions that evoke feelings of security at home. Stimuli most often selected by the test subjects are thus validated against the model and useful for future testing, while stimuli that are less often or not selected are presumed to be not representative of the motive.

Another exemplary process for classifying stimuli (e.g., images) is to provide one or more investigators with a set of image cues with instructions to find related images at their best discretion by searching, for example, their environment, a library, or the Internet. The images which are found are then tested and validated by exposing the images to a large sample, asking each respondent in the sample to match each image with an emotional category, and selecting those images where a statistically significant majority of respondents associate a particular image with a particular emotion. Validation may be performed, for example, across an entire matrix simultaneously, or, on a single matrix dimension at a time.

Another exemplary process for classifying images includes inserting prospective emotive images into a sequence of classified images during a stimulus test performed in accordance with embodiments of the present disclosure. The prospective images may be classified by association using any of the comparison methods described herein. For example, in a set of five images each representing one emotion, three of the images are vetted and two are not. If multiple test subjects exposed to all five images select either or both of the unvetted images along with one or more of the vetted images, the unvetted images can be vetted or classified using statistical analysis of the cumulative selections by all test subjects. Over a period of many tests and a variety of topics a valid classification of the image may emerge.

According to another embodiment, a comparison of emotional responses by multiple individuals to various stimuli may be performed using a "crowd-sourcing" theory. For example, the individuals may select images of products that have emotional appeal to them, e.g., an individual may be asked to select their favorite type of literature by selecting from a group of books including books that the subject has looked at and books that other subjects have looked at. Over time, one or more clusters of images representing the collective responses of the individuals are formed. The cluster(s) may be statistically analyzed to identify a common emotional theme among the images, which may then be classified according to that emotion.

Testing System

Figure 10:
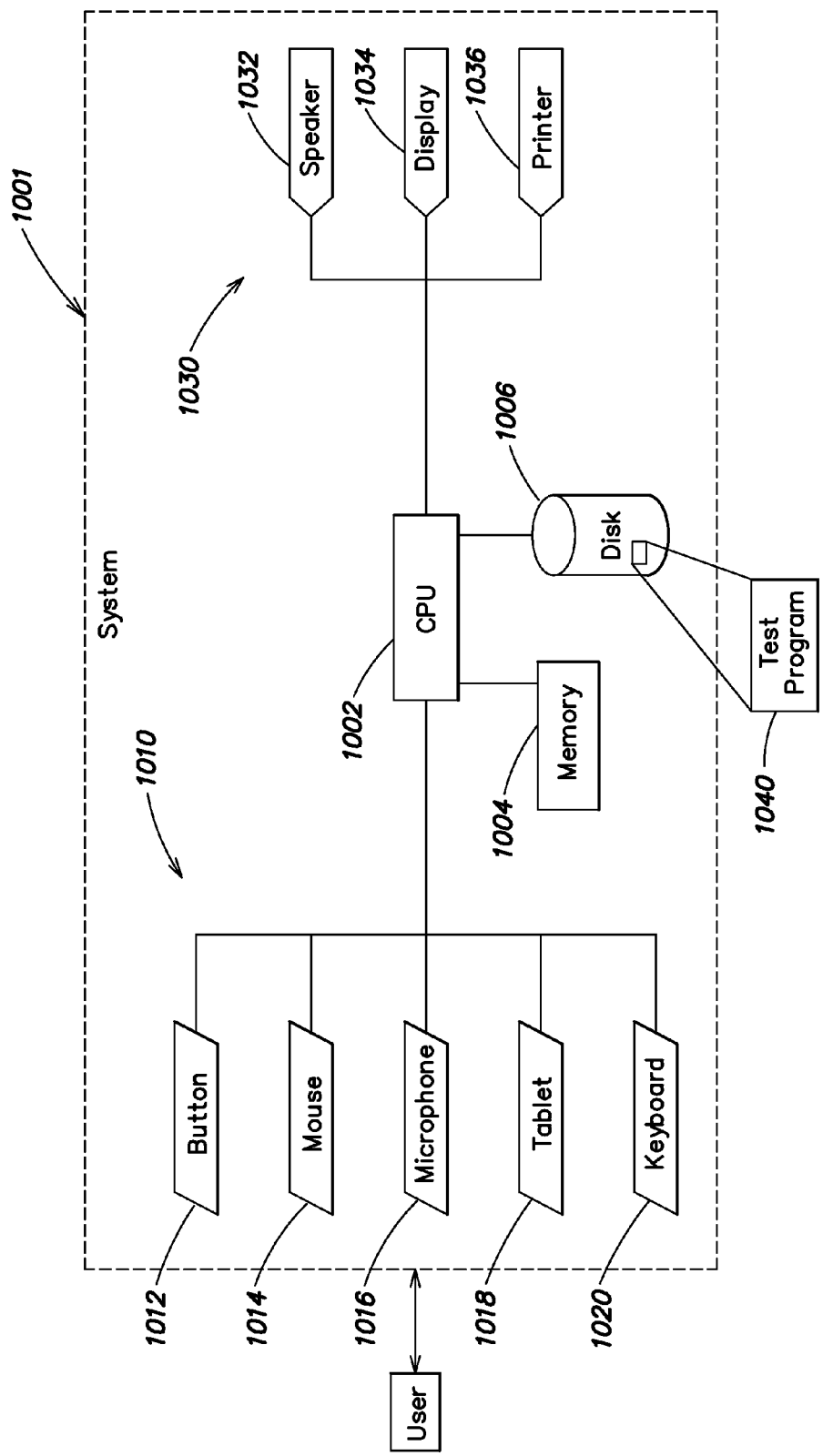
FIG. 10 illustrates an exemplary system in which various embodiments of the disclosure may be implemented.

FIG. 10 shows an exemplary system architecture of the present disclosure, which is generally indicated at 1001. A central computer 1002, or CPU, is connected to memory 1004 and disk storage 1006. A nonexclusive list of input devices, generally indicated at 1010, are connected to the CPU 1002, including (but not limited to) a button 1012, a mouse 1014 or similar pointing device, a microphone 1016, a tablet 1018, and a keyboard 1020. A nonexclusive list of output devices, generally indicated at 1030, are also connected to the CPU 1002, including (but not limited to) a speaker 1032, a display 1034, and a printer 1036. It should be appreciated that a computer system used to implement various embodiments of the present invention may include other types of input/output devices or have a different architecture than the computer shown.

One embodiment of the invention may be embodied by software stored on a computer-readable medium (e.g., a memory, storage, disc or other medium), and executed by one or more computer systems. In one embodiment, a test program 1040 is stored on the disk 1006. For instance, various embodiments can be executed by a computer system having an architecture as shown in FIG. 10.

Figure 11:
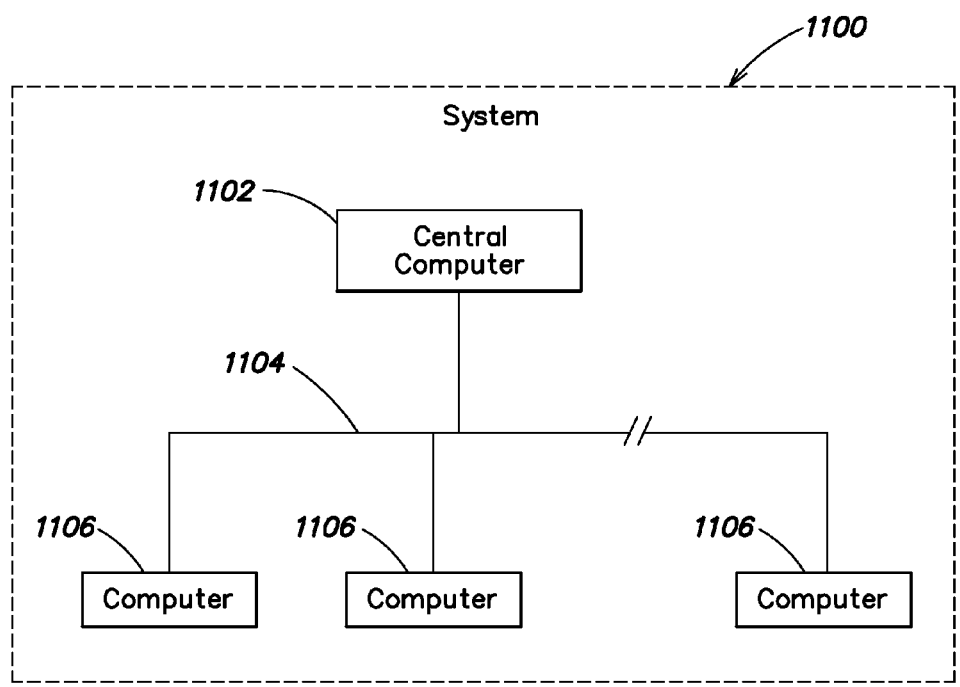
FIG. 11 illustrates an exemplary system in which various embodiments of the disclosure may be implemented.

Referring to FIG. 11, an exemplary system architecture of a distributed testing system in accordance with the present disclosure is generally indicated at 1100. A central computer 1102 is connected to a wired or wireless network 1104. One or more fixed or portable computing systems 1106 are also connected to the wired or wireless network 1104, so that they may communicate with the central computer 1102. The types of computing systems 1106 may include, but is not limited to, handheld personal digital assistants (PDAs), desktop personal computers (PCs), laptop PCs, tablet PCs, game controllers, "smart" phones, and the like. In one example, responses from one or more respondents in a focus group session or in a survey may simultaneously gathered using the computers 1106 (e.g., a cell phone, PDA, tablet computer or other type of portable computer system) connected wirelessly to the central computer 1102 over the network 1104. The central computer 1102 may analyze the responses in real time and provide further outputs to be presented to a moderator and/or each respondent for further probing and discussion among the focus group.

In another example, focus group interviews may be conducted whereby a moderator and one or more respondents utilize computers 1106 connected to the central computer 1102 over a network 1104. In one embodiment, the system allows all members of the group to make inputs simultaneously to a single database or a single computerized "object" (e.g., a photo collage) stored in memory or on disk utilizing one or more input devices. In conjunction with output devices, all members of the group may work with the results generated collectively by the group as a basis for continued discussion and reflection.

In another example, focus group interviews are conducted where a third party may observe and/or participate in the research in real time. A moderator, the third party, and one or more respondents utilize computers connected to the central computer over the network. For instance, computers may be any type of computer systems as discussed above, including, but not limited to, portable computers such as laptops, cell phones, PDAs, or other types of computer systems. The system allows all members of the group to make inputs simultaneously to a single database or a single computerized "object" (e.g., a photo collage) stored in memory or on disk utilizing one or more of the input devices. In conjunction with output devices, all to members of the group may work with the results generated collectively by the group as a basis for continued discussion and reflection.

Utilizing the exemplary system architecture described above in FIG. 11, several applications of the present disclosure may be implemented. In one example, the disclosed method may be used to expose photo-stimuli (for, e.g., a one second exposure time or similar period sufficient to invoke an emotional response, but not to give the respondent time to form a well-thought response) to force emotionally-driven selections of photos that associate with the emotional states of the respondents. Photo selections made by all members of a focus group are scored by the total number of votes, and by the speed of selection (response time) to generate a list of "most salient" stimuli that are probed in more detail to uncover information about emotional states.

Example Applications

The following is a non-limiting list of applications in accordance with embodiments of the present disclosure. Various embodiments of the present disclosure may be used for qualitative market research, including focus group testing and interviewing; quantitative market research, including surveys; company performance assessment and human resources performance evaluations; hiring testing; clinical testing, including mental health assessment; military intelligence; product and service rating polls; political or public polling; consumer experience measurement; exit polls; consumer product testing; consumer profiling; and advertising classification by motivational impact.

In another example, the disclosed method may be used to assess the positive and negative reactions of individuals to a video or audio stimulus on a second-by-second basis, capturing these reactions and displaying them to a focus group (e.g., a "dial" or strength test). Stimuli are then reviewed alongside a visual graphic display of positive and negative reactions (like a "brain-wave readout"), enabling the group to focus on and discuss the reasons underlying the patterns in the moment-to-moment reactions.

In one example, embodiments of the present disclosure may be used to assess aspirations of one or more consumers with respect to a particular consumer product, to either through interviews, surveys, testing, or a combination thereof. The results of the assessment may then be used, for example, by a manufacturer to strategically develop a marketing campaign targeting the consumer's aspirations, or to develop new products which are better at delivering on consumers' aspirations.

In another example, embodiments of the present disclosure may be used to assess emotional characteristics of one or more employees. The results of the assessment may then be used, for example, by an employer to strategically develop one or more work teams comprising employees having compatible emotional characteristics.

In another example, embodiments of the present disclosure may be used to identify the characteristics of test subjects who are interviewed, surveyed, and/or tested during market research.

In another example, embodiments of the present disclosure may be used to assess a candidate for employment during the hiring process. For example, a candidate may take a test in accordance with the present disclosure. The results of the test may then be used to choose or avoid the candidate based on the quantitative emotional profile of the candidate.

In another example, embodiments of the present disclosure may be used to screen a person for certain mental health conditions, perform diagnostic mental health testing, or develop a therapeutic treatment strategy for a patient.

In another example, embodiments of the present disclosure may be used to develop a military strategy. For example, a test in accordance with the present disclosure may be administered to a person in one place (e.g., in a country having rival factions), and the results compared with the results of similarly-tested people from another place to determine if that person is likely to harbor sentiments possessed by people in the other place (e.g., a member of the rival faction).

In another example, embodiments of the present disclosure may be used to perform product surveys on product experience, impression and reputation from an emotional point of view.

In another example, embodiments of the present disclosure may be used to survey voters after viewing or hearing a political speech or presentation to develop a to political campaign strategy. For example, the campaign strategy may be developed to appeal to the motives elicited by a test conducted in accordance with one embodiment of the present disclosure.

In another example, embodiments of the present disclosure may be used to perform secret shopper testing.

In another example, embodiments of the present disclosure may be used to conduct exit polls of voters.

In another example, embodiments of the present disclosure may be used to evaluate a product against similar products, and to further design the product to meet the consumers' aspirations with respect to the similar products.

In another example, embodiments of the present disclosure may be used to perform reverse emotional engineering. For example, the results of a test conducted in accordance with one embodiment of the present disclosure may be used to develop a product that matches a consumer's aspiration to use a competing product (e.g., a high-end luxury product).

In another example, embodiments of the present disclosure may be used to classify advertisements by motivational category (i.e., instead of by topic), and then develop and present advertising having the same motivational category as those most often read by a consumer (e.g., web-based advertising).

In another example, embodiments of the present disclosure may be used to profile a prospective customer and adapt a marketing strategy based on the profile (e.g., identify the aspirations of a new car buyer to market the appropriate car to them).

In another example, embodiments of the present disclosure may be used to develop a fraud management strategy. For example, a disability insurance claimant may be profiled with respect to his attitude toward his job, and a predictive algorithm for identifying claimants who are likely to defraud insurers by not returning to their jobs when disability has diminished may be developed. Other types of fraud may be managed, including attempts by the subject to subvert the stimulus test.

In another example, embodiments of the present disclosure may be used to to detect fraud or subversion of the test. For example, if the subject responds to none of the stimuli, there is no useful information for assessing the subject's emotional characteristics. Likewise the results of the test are likely to be skewed if the subject responds to the stimuli in a predictable pattern, for example by selecting every third image in the sequence or in a repeated pattern, selecting images randomly, selecting only images containing a certain color or object, or selecting all images in the set.

Having thus described several embodiments of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method comprising:
presenting, by a computer through a presentation interface, stimuli to a subject, including, for each stimulus:
presenting the stimulus for a limited period of time, the duration of the limited period being enforced by computer to have a predefined duration of more than 500 milliseconds and less than 1000 milliseconds, the duration of the limited period of time being insufficient to enable conscious cognitive reflection on the stimulus by the subject,
ending the presenting of the stimulus at the end of the limited period of time,
providing a computer-enforced grace period immediately following the end of the limited period of time, the computer-enforced grace period having a predefined duration of up to 300 milliseconds during which the stimuli are not presented, and
presenting a subsequent stimulus at the end of the computer-enforced grace period;
in response to presenting at least one of the stimuli, receiving, by a computer, within a response period that includes the limited period of time and the computer-enforced grace period, an emotional response from the subject indicative of a pre-cognitive emotional reaction of the subject to the stimulus, the duration of the response period of time being insufficient to enable conscious cognitive reflection on the stimulus by the subject; and
determining, by a computer, a quantitative representation of an emotional profile of the subject based on at least the emotional response.

2. The method set forth in claim 1, wherein each of the stimuli comprises one or more of an image, a sound, a color, a smell, or a texture.

3. The method set forth in claim 1, wherein each stimulus is statistically associated with at least one emotional characteristic, and comprising determining the quantitative emotional profile of the subject based on the at least one emotional characteristic associated with each stimulus for which an emotional response was received from the subject.

4. The method set forth in claim 1, comprising providing, to the subject, at least one prompt related to a research topic.

5. The method set forth in claim 4, wherein providing the at least one prompt includes providing a matter at hand.

6. The method set forth in claim 4, wherein providing the at least one prompt includes providing a stem sentence.

7. The method set forth in claim 1, comprising loading a stimulus set including stimuli.

8. The method set forth in claim 1, comprising recording the emotional response.

9. The method set forth in claim 1, comprising recording a reaction time of the subject for the emotional response.

10. The method set forth in claim 1, comprising determining the quantitative emotional profile based on a reaction time of the subject for the emotional response.

11. The method set forth in claim 1, comprising determining the quantitative emotional profile based on a number of stimuli for which an emotional response was received from the subject.

12. The method set forth in claim 1, comprising determining the quantitative emotional profile based on an emotion statistically associated with each stimulus for which an emotional response was received from the subject.

13. The method set forth in claim 1, wherein determining the quantitative emotional profile comprises comparing the emotional response for a first one of the stimuli to an emotional response for a second one of the stimuli.

14. The method set forth in claim 1, comprising:
presenting, to the subject, in a rapid exposure sequence, each of the stimuli for which a response was received from the subject, and
measuring a biometric response of the subject to at least one of the stimuli.

15. The method set forth in claim 1, comprising developing an element of a marketing campaign based on the quantitative emotional profile.

16. The method set forth in claim 1, comprising developing an aspect of a consumer product based on the quantitative emotional profile.

17. The method set forth in claim 1, comprising developing one or more work teams based on the quantitative emotional profile.

18. The method set forth in claim 1, comprising developing an element of a fraud management strategy based on the quantitative emotional profile.

19. The method set forth in claim 1, comprising developing an element of a therapeutic treatment strategy based on the quantitative emotional profile.

20. The method set forth in claim 1, comprising classifying an advertisement based on the quantitative emotional profile.

21. The method set forth in claim 1, comprising developing an element of a political campaign strategy based on the quantitative emotional profile.

22. The method set forth in claim 1, wherein the stimulus is gradually removed from presentation starting at the end of the limited period of time.

23. The method of claim 1, wherein the duration of the response period of time is sufficient to enable only precognitive emotional evaluation, by the subject, of how the stimulus makes the subject feel, without enabling conscious cognitive reflection on the stimulus by the subject.

24. The method of claim 1, in which the emotional response is received between 800 and 1300 seconds after beginning presentation of the stimulus.

25. A non-transitory computer readable medium comprising computer-executable instructions that cause a processor to:
present stimuli to a subject through a presentation interface, including, for each stimulus:
presenting the stimulus for a limited period of time, the duration of the limited period being enforced by computer to have a predefined duration of more than 500 milliseconds and less than 1000 milliseconds, the duration of the limited period of time being insufficient to enable conscious cognitive reflection on the stimulus by the subject,
ending the presenting of the stimulus at the end of the limited period of time,
providing a computer-enforced grace period immediately following the end of the limited period of time, the computer-enforced grace period having a predefined duration of up to 300 milliseconds during which the stimuli are not presented, and
presenting a subsequent stimulus at the end of the computer-enforced grace period;
in response to presenting at least one of the stimuli, receiving, within a response period that includes the limited period of time and the computer-enforced grace period, an emotional response from the subject, the duration of the response period of time being insufficient to enable conscious cognitive reflection on the stimulus by the subject; and
determining a quantitative representation of an emotional profile of the subject based on at least the emotional response.

26. A method comprising:
selecting, by a computer, an emotion based on a quantitative emotional profile of a subject;
providing, to the subject, by a computer through a presentation interface, a prompt relating to a topic;
presenting, to the subject, by a computer through the presentation interface, a group of at least two descriptor words associated with the emotion, the presenting including:
presenting the group of at least two descriptor words for a limited period of time, the duration of the limited period being enforced by computer to have a predefined duration of more than 500 milliseconds and less than 1000 milliseconds, the duration of the limited period of time being insufficient to enable conscious cognitive reflection on the at least two descriptor words by the subject,
ending the presenting of the group of at least two descriptor words at the end of the limited period of time, and
providing a computer-enforced grace period immediately following the end of the limited period of time, the computer-enforced grace period having a predefined duration of up to 300 milliseconds during which the group of at least two descriptor words is not presented;
recording, by a computer, a selection, by the subject, of a subset of the group of descriptor words, the selection received from the subject during a response period that includes the limited period of time and the computer-enforced grace period, the duration of the response period of time being insufficient to enable conscious cognitive reflection on the at least two descriptor words by the subject;
presenting, by a computer, one or more other groups each of at least two descriptor words associated with the emotion, including presenting a subsequent group of at least two descriptor words at the end of the computer-enforced grace period of a prior group of at least two descriptor words;
recording, by a computer, a selection, by the subject, of a subset of each of the other groups of descriptor words; and
refining, by a computer, the quantitative representation of an emotional profile of the subject based on the selections by the subject.

27. A method comprising:
assigning, by a computer, each of one or more emotional characteristics to a corresponding element of a matrix, in which each of one or more stimuli has been statistically associated with one of the elements;

presenting, to a subject by a computer through a presentation interface, one of the stimuli and a prompt, the presenting of the one of the stimuli including:
  presenting the one of the stimuli for a limited period of time, the duration of the limited period being enforced by computer to have a predefined duration of more than 500 milliseconds and less than 1000 milliseconds, the duration of the limited period of time being insufficient to enable conscious cognitive reflection on the stimulus by the subject;
  ending the presenting of the one of the stimuli at the end of the limited period of time; and
  providing a computer-enforced grace period immediately following the end of the limited period of time, the computer-enforced grace period having a predefined duration of up to 300 milliseconds during which the one or more stimuli are not presented;
recording, by a computer, a classification by the subject of the one of the stimuli into one of the elements, an input indicative of the classification having been received from the subject during a response period that includes the limited period of time and the computer-enforced grace period, the duration of the response period of time being insufficient to enable conscious cognitive reflection on the stimulus by the subject;
repeating, by a computer, the presenting and recording for each of the stimuli, including presenting a subsequent stimulus at the end of the computer-enforced grace period of a prior stimulus; and
identifying, by a computer, for each of the stimuli, one or more emotional characteristics for which the classification by the subject matches an initial classification of the stimulus.

28. The method set forth in claim 27, wherein each of the stimuli comprises one or more of an image, a sound, a color, a smell, or a texture.

29. A method comprising:
presenting, by a computer through a presentation interface, a stimulus to a group of subjects, including:
  presenting the stimulus to each subject for a limited period of time, the duration of the limited period being enforced by computer to have a predefined duration of more than 500 milliseconds and less than 1000 milliseconds, the duration of the limited period of time being insufficient to enable conscious cognitive reflection on the stimulus by the subject;
  ending the presenting of the stimulus at the end of the limited period of time;
  providing a computer-enforced grace period immediately following the end of the limited period of time, the computer-enforced grace period having a predefined duration of up to 300 milliseconds during which the stimulus is not presented;
recording, by a computer, a response for each subject of the group, the response including a selection representing the stimulus and a reaction time, the response having been received within a response period that includes the limited period of time and the computer-enforced grace period, the duration of the response period being insufficient to enable conscious cognitive reflection on the stimulus by the subject;
repeating, by a computer, the presenting and recording for one or more other stimuli, including presenting a subsequent stimulus at the end of the computer-enforced grace period of a prior stimulus; and
identifying, from the group of subjects, subjects who have a similar emotional characteristic based on the responses.

30. The method set forth in claim 29, wherein each of the stimuli comprises one or more of an image, a sound, a color, a smell, or a texture.

31. The method set forth in claim 29, comprising identifying a cluster of stimuli based on the responses.

32. The method set forth in claim 31, comprising
presenting, to one or more other subjects, each of the stimuli in the cluster of stimuli, and
receiving a description of a feeling evoked in each of the subjects by each of the stimuli.

33. A method comprising:
presenting, by a computer through a presentation interface, visual stimuli to a subject, including, for each visual stimulus:
  presenting the stimulus for a limited period of time, the duration of the limited period being enforced by computer to have a predefined duration of more than 500 milliseconds and less than 1000 milliseconds, the duration of the limited period of time being insufficient to enable conscious cognitive reflection on of the stimulus by the subject;
  ending the presenting of the visual stimulus at the end of the limited period of time;
  providing a computer-enforced grace period immediately following the end of the limited period of time, the computer-enforced grace period having a predefined duration of up to 300 milliseconds during which the visual stimuli are not presented and
  presenting a subsequent visual stimulus at the end of the computer-enforced grace period,
in response to presenting at least one of the visual stimuli, receiving, by a computer, within a response period that includes the limited period of time and the computer-enforced grace period, feedback from the subject that comprises a response indicative of an emotional state of the subject in relation to a topic, the duration of the response period being insufficient to enable conscious cognitive reflection on the stimulus by the subject; and
determining, by a computer, an quantitative measurement of an emotional characteristic of the subject based on the feedback.

34. A method comprising:
presenting, by a computer through a presentation interface, stimuli to a subject, including, for each stimulus:
  presenting the stimulus for a limited period of time, the duration of the limited period being enforced by computer to have a predefined duration of less than one second, the duration of the limited period of time being insufficient to enable conscious cognitive reflection on the stimulus by the subject;
  ending the presenting of the stimulus at the end of the limited period of time;
  providing a computer-enforced grace period immediately following the end of the limited period of time, the computer-enforced grace period having a predefined duration of up to 300 milliseconds during which the stimuli are not presented; and
  presenting a subsequent stimulus at the end of the computer-enforced grace period;
receiving, by a computer, an emotional response of the subject to at least one of the stimuli within a response period that includes the limited period of time and the computer-enforced grace period, the duration of the response period being insufficient to enable conscious cognitive reflection on the stimulus by the subject; and determining a quantitative representation of an emotional profile of the subject based on at least the emotional response.

35. The method of claim 34, comprising presenting each stimulus for between 500 milliseconds and one second.

36. The method set forth in claim 34, in which receiving the emotional response includes receiving the emotional response to a particular stimulus during presentation of the particular stimulus.

37. The method set forth in claim 34, in which receiving the emotional response includes receiving the emotional response to a particular stimulus after the particular stimulus is removed from presentation.

38. The method set forth in claim 37, in which receiving the emotional response includes receiving the emotional response within 300 milliseconds after the particular stimulus is removed from presentation.

* * * * *